United States Patent
Krill et al.

(10) Patent No.: US 11,731,931 B2
(45) Date of Patent: Aug. 22, 2023

(54) PROCESS FOR PURIFYING METHYL METHACRYLATE OF LOW-BOILING COMPONENTS

(71) Applicant: Röhm GmbH, Darmstadt (DE)

(72) Inventors: Steffen Krill, Muehltal (DE); Daniel Helmut König, Stuttgart (DE); Belaid Ait Aissa, Darmstadt (DE)

(73) Assignee: Röhm GmbH, Darmstadt (DE)

( * ) Notice: Subject to any disclaimer, the term of this patent is extended or adjusted under 35 U.S.C. 154(b) by 7 days.

(21) Appl. No.: 17/754,096

(22) PCT Filed: Sep. 10, 2020

(86) PCT No.: PCT/EP2020/075351
§ 371 (c)(1),
(2) Date: Mar. 23, 2022

(87) PCT Pub. No.: WO2021/058293
PCT Pub. Date: Apr. 1, 2021

(65) Prior Publication Data
US 2022/0388942 A1 Dec. 8, 2022

(30) Foreign Application Priority Data
Sep. 25, 2019 (EP) .................................. 19199547

(51) Int. Cl.
*C07C 67/54* (2006.01)
*C07C 67/44* (2006.01)
(Continued)

(52) U.S. Cl.
CPC ................ *C07C 67/54* (2013.01); *B01D 3/14* (2013.01); *C07C 45/75* (2013.01); *C07C 67/44* (2013.01); *C07C 67/60* (2013.01); *C07C 67/62* (2013.01)

(58) Field of Classification Search
CPC ......... C07C 67/44; C07C 67/54; C07C 67/60; C07C 67/62; C07C 45/75
See application file for complete search history.

(56) References Cited

U.S. PATENT DOCUMENTS

| 4,070,254 A | 1/1978 | Sato et al. |
| 4,518,462 A | 5/1985 | Aoshima et al. |

(Continued)

FOREIGN PATENT DOCUMENTS

| WO | 2014/170223 | 10/2014 |
| WO | 2017/046110 | 3/2017 |

OTHER PUBLICATIONS

International Search Report dated Nov. 10, 2020 in PCT/EP2020/075351, with English Translation, 5 pages.
(Continued)

*Primary Examiner* — Yate' K Cutliff
(74) *Attorney, Agent, or Firm* — Grüneberg and Myers PLLC

(57) ABSTRACT

A novel process can be used for purifying methyl methacrylate (MMA) contaminated with low-boiling components by distillation, where the process involves producing MMA by oxidative esterification, and a crude product containing methyl propionate (MP), methyl isobutyrate (MIB), and methacrolein (MAL) as low-boiling components. The process is compatible with MMA produced from $C_2$-based methacrolein containing the low-boiling components specified.

15 Claims, 2 Drawing Sheets

(51) Int. Cl.
   *C07C 67/60*   (2006.01)
   *C07C 67/62*   (2006.01)
   *C07C 45/75*   (2006.01)
   *B01D 3/14*    (2006.01)

(56) References Cited

U.S. PATENT DOCUMENTS

| | | |
|---|---|---|
| 5,969,178 A | 10/1999 | Okamoto et al. |
| 7,012,039 B2 | 3/2006 | Watanabe et al. |
| 9,617,199 B2 | 4/2017 | Krill et al. |
| 9,890,105 B2 | 2/2018 | Krill et al. |
| 10,301,251 B2 | 5/2019 | Groemping et al. |
| 10,479,754 B2 | 11/2019 | Krill et al. |
| 11,124,471 B2 | 9/2021 | Lygin et al. |
| 2016/0068464 A1* | 3/2016 | Krill ................... C07C 67/39 560/208 |
| 2016/0251301 A1 | 9/2016 | Krill et al. |
| 2018/0251418 A1 | 9/2018 | Krill et al. |
| 2018/0251419 A1* | 9/2018 | Groemping ............ C07C 45/28 |
| 2021/0032386 A1 | 2/2021 | Krill et al. |
| 2021/0047259 A1 | 2/2021 | Lygin et al. |
| 2021/0269385 A1 | 9/2021 | Krill et al. |

OTHER PUBLICATIONS

Written Opinion received dated Nov. 10, 2020 in PCT/EP2020/075351, with English Translation, 8 pages.

U.S. Appl. No. 16/637,575, filed Feb. 7, 2020, 2021/0032386, Krill et al.

U.S. Appl. No. 17/250,260, filed Dec. 22, 2020, 2021/0269385, Krill et al.

\* cited by examiner

PROCESS FOR PURIFYING METHYL METHACRYLATE OF LOW-BOILING COMPONENTS

CROSS-REFERENCE TO RELATED APPLICATIONS

This application is the National Stage entry under § 371 of International Application No. PCT/EP2020/075351, filed on Sep. 10, 2020, and which claims the benefit of European Application No. 19199547.1, filed on Sep. 25, 2019. The content of each of these applications is hereby incorporated by reference in its entirety.

BACKGROUND OF THE INVENTION

Field of the Invention

The present invention relates to a novel process for purifying methyl methacrylate (MMA) contaminated with low-boiling components by distillation, wherein said MMA was produced by oxidative esterification, and as crude product comprises methyl propionate (MP), methyl isobutyrate (MIB) and methacrolein (MAL) as low-boiling components. The process in this case is applicable to MMA produced from C2-based methacrolein comprising the low-boiling components specified. However, the process can also theoretically be transferable to MMA produced from C4-based methacrolein, which comprises MP and MAL but no notable amounts of MIB.

Description of Related Art

Methyl methacrylate (MMA) is today produced by a very wide variety of processes proceeding from $C_2$-, $C_3$- or $C_4$-building blocks. In one of these processes, MMA is obtained by a direct oxidative esterification reaction of methacrolein using methanol. In this case, methacrolein is obtained in the first stage from propanal and formaldehyde. Such a process is described in WO 2014/170223.

The process according to the invention comprises the preparation of methacrolein according to the so-called C2 method from formalin and propionaldehyde in the presence of a secondary amine and an acid, usually an organic acid. The reaction takes place in this case via a Mannich-like reaction with subsequent release of the catalytic secondary amine. Such processes for the preparation of methacrolein are described, inter alia, in documents U.S. Pat. Nos. 7,141,702, 4,408,079, JP 3069420, JP 4173757, EP 0317909 and U.S. Pat. No. 2,848,499. Depending on the method, yields between 91 and 98% can be achieved. A methacrolein stream is generally obtained comprising a propionaldehyde content between 100 ppm and 2% by weight alter purification. This methacrolein quality is in principle suitable for subsequent conversion to MMA by direct oxidative esterification of the methacrolein in the liquid phase.

The preparation of MMA from methacrolein in the so-called direct oxidative esterification in the liquid phase with air and methanol as reactants and the subsequent purification of the crude MMA is of particular significance for the present invention.

The documents U.S. Pat. Nos. 5,969,178, 7,012,039, WO 2014/170223 and WO 2017/046110 describe the process of producing MMA by means of oxidative esterification. Disclosed here are different process control options for feeding methacrolein to the oxidative esterification and also the processing of the crude MMA obtained. For the process according to the invention, the process variant preferred in this case is that in which fresh methacrolein is mixed with the reactor output of the oxidative esterification and is separated by fractionation such that present in the distillate are methacrolein, propionaldehyde, further secondary components which have a lower boning point than methacrolein, and a portion of the methanol. In particular, other process variants are also conceivable for the process according to the invention, particularly those in which propionaldehyde from the methacrolein synthesis in the process step of oxidative esterification is converted to methyl propionate. The bottom fraction of this fraction preferably comprises MMA, water, methacrylic acid, salts, MIB, MP and further organic high-boilers. The process variant has been described in WO 2017/048110. Furthermore, according to the process according to the invention, methyl propionate is formed in the oxidative esterification of propionaldehyde. In addition, methyl isobutyrate is formed. Typically, after extraction, crude MMA is processed using two or more distillation columns. This crude MMA comprises, for example, methacrolein, methyl propionate, methyl isobutyrate, methanol, water, methacrylic acid and high-boiling secondary components. The processing concepts according to the prior art may well lead to methyl methacrylate of good quality but these exhibit elevated trace amounts of the critical and secondary components, methyl propionate and methyl isobutyrate, that are difficult to remove.

U.S. Pat. No. 4,518,482 discloses a process for producing MMA in which, from an oxidative esterification of methacrolein or an esterification of methacrylic acid, removal of methyl isobutyrate (MIB) from the crude MMA is carried out with hexane as entrainer. The feed to the accompanying distillation column comprises in this case methanol, MMA, water from the reaction and MIB. The distillation is carried out without further supply of water. The separating principle underlying this distillation is that the hexane entrainer breaks up the azeotrope formed from MMA and methanol. However, this procedure does not show any effect on the azeotrope formed by MIB and methanol. As a consequence, MIB is enriched in the top of the column, while purified MMA is removed in the bottoms and water is withdrawn in a side stream. In a subsequent phase separation of the distillate, hexane is obtained as main constituent of the organic phase and methanol and MIB as constituents of a polar phase. A subsequent second distillation of this polar phase is carried out to remove the residual hexane and other low-boiling components from the methanol, but where MIB remains in the methanol phase. To recycle the methanol to the reactor would therefore require a third, very laborious distillation of this stream. U.S. Pat. No. 4,518,482 specifies an MMA recovery, depending on operating conditions, of between 95.4 and 98.2%. In this case, the MMA purity, depending on the mode or operation, is between 98.38% by weight and 99.9% by weight.

U.S. Pat. No. 4,070,254 describes a process for producing MMA by, for example, an oxidative esterification of a C4-based methacrolein or another method. The removal of MP from MMA is also not described here. The process foregoes the use of an entrainer. The distillative separation requires very many stages overall. The separating concept here is based on a feed comprising MMA and MIB and also optionally water being firstly distilled into the distillate in one or two columns with decanter. In this case, additional water may be added either in the decanter or In the column feed. The separating principle is the enrichment of MIB in the tops of the columns. In this case, a partial separating off of the MIB into the respective water phase takes place, which each time results in a relevant loss of MMA. An important control parameter is the water addition in terms of the ratio to the MIB content in the feed. The loss of MMA can be reduced by optimization but cannot be avoided. The organic stream of the decanter of the second column occurs as a waste stream or can optionally be distilled in one process variant in a third column, wherein MMA is recovered as bottoms of the columns. However, this process variant—particularly with regard to the energy demand and the required number of separation apparatuses—is very costly. Depending on the mode of operation, the process achieves an MMA purity between 98.99% by weight and 99.70% by weight. The MMA recovery is between 95.0 and 98.94%.

SUMMARY OF THE INVENTION

Objects

The object of the present invention was to provide a novel process for processing alkyl methacrylate produced from methacrolein, from which low-boiling by-products are particularly efficiently removed.

In particular, it was the object in this case to implement this by means of a novel distillation integrated into the processing of the alkyl methacrylate.

The alkyl methacrylate is particularly preferably MMA. Therefore, the object in this case was to particularly efficiently remove methyl propionate MP, methyl isobutyrate MIB and methacrolein MAL from said MMA with the lowest possible energy demand.

Furthermore, it was an object of the present invention that the novel method can be applied to the purification of alkyl methacrylates which have been produced from methacrolein, independently of whether the alkyl methacrylate has been obtained from methacrolein via an oxidative esterification or an oxidation with subsequent esterification. Here in particular, by-products should be removed which are present in MMA which has been produced from methacrolein from a C2 source.

Further non-explicit objects may arise from the examples or the description, as well as from the overall context of the invention, also with respect to the prior art.

Solution

These objects were achieved by a novel process for producing alkyl methacrylates in which methacrolein is produced in a first reaction stage in a reactor I, and this is esterified oxidatively with an alcohol in the presence of an oxygen-containing gas in a second reaction stage in a reactor II, resulting in an unpurified alkyl methacrylate stream. This novel process is characterized in particular by the following process aspects:

a. in reactor I, starting from propionaldehyde and formalin, methacrolein is obtained. In this case, this methacrolein comprises propionaldehyde.
b. In reactor II and an optional reactor III, the propionaldehyde present in the methacrolein is then converted to an alkyl propionate. At the same time. In at least one of these reactors, an alkyl isobutyrate is formed.
c. after reactor II or reactor III, the resulting crude alkyl methacrylate stream is processed in a work-up process to give pure alkyl methacrylate. In this case, this work-up process passes through two or more distillative separation columns and at least one extractive separation. At the start, the crude alkyl methacrylate stream in this case comprises alkyl propionate and alkyl isobutyrate.

DETAILED DESCRIPTION OF THE INVENTION

In accordance with the invention, process step c has at least one distillation column I in which alkyl methacrylate is separated off as the bottom fraction. In this case, by means of fractionation, the by-product fraction comprising methacrolein, and alkyl isobutyrate and/or alkyl propionate, is obtained as the overhead fraction.

There are two preferred embodiments of the present invention. In the first of these embodiments, reactor II is a reactor in which MAL is oxidatively esterified with an alcohol and oxygen to give the alkyl methacrylate. This reaction is preferably carried out in the liquid phase and catalyzed with noble metal-containing catalysts. In this embodiment, there is no reactor III.

In the second embodiment, MAL is oxidized to methacrylic acid in reactor II—preferably in a gas phase. This is followed in reactor III by esterification of this methacrylic acid with an alcohol to give the alkyl methacrylate. This stage in reactor III preferably takes place in a liquid phase.

Preferably, in process step c of the process according to the invention, an alkyl methacrylate is obtained having a respective content or alkyl propionate and alkyl isobutyrate of less than 0.1% by weight.

In general, the alcohol used in the process according to the invention is methanol. Accordingly, the alkyl methacrylate is MMA, the alkyl isobutyrate is methyl isobutyrate and the alkyl propionate is methyl propionate.

Figure 1:
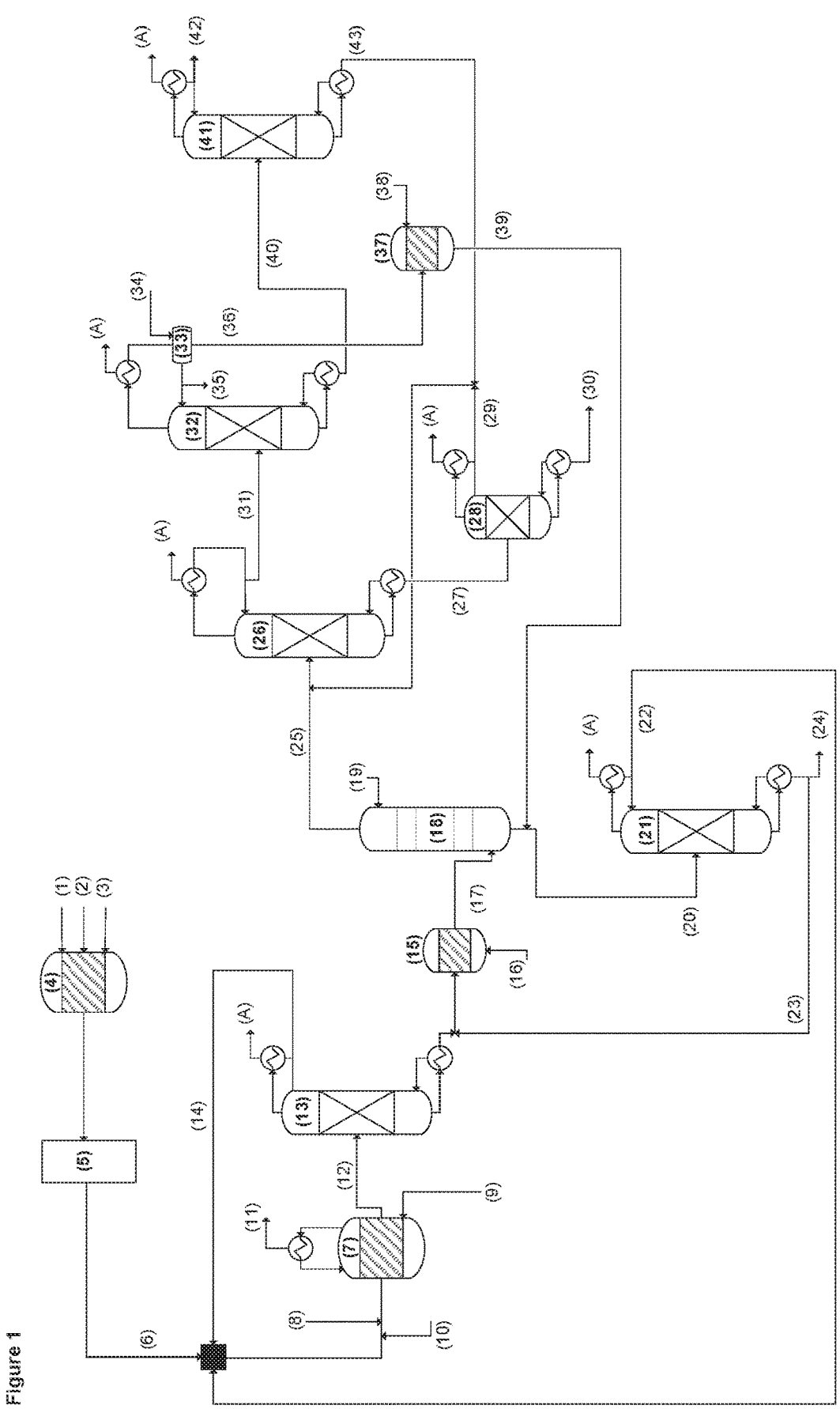
FIG. 1 shows an overall flow diagram of the production of MMA starting from formalin and propanal.

In this variant, the overhead fraction of distillation column I is conveyed to a phase separator I and is separated therein into an aqueous and an organic fraction (see FIG. 1). Particularly preferably in this case, additional water is conveyed into this phase separator I, wherein the water may be fresh water and/or a water-containing recycling stream from one or more other process steps.

It is also preferred that the organic phase from phase separator I, comprising the by-products methacrolein, alkyl isobutyrate and alkyl propionate, is partially or wholly recycled to distillation column I.

Figure 2:
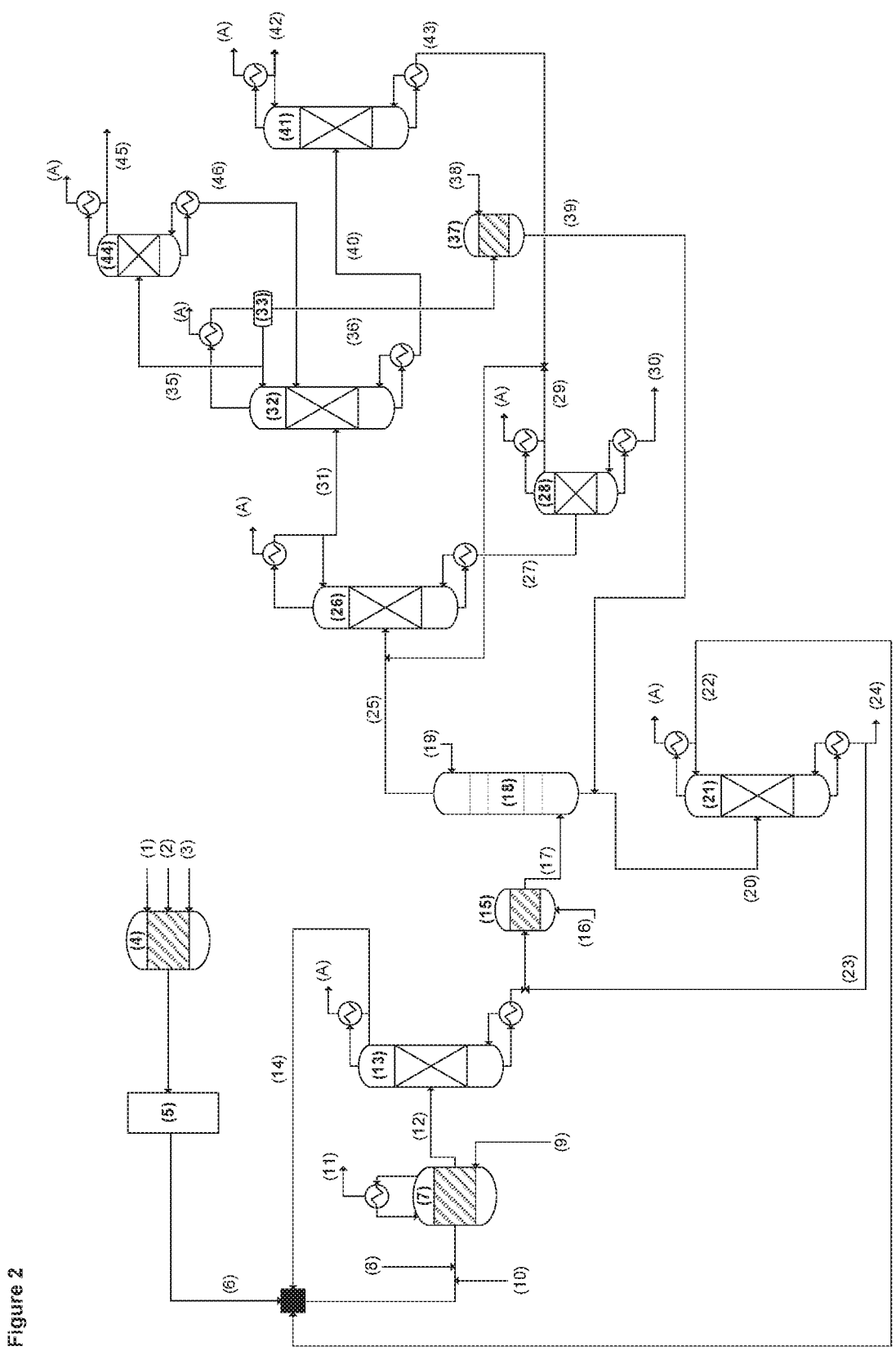
FIG. 2 shows an overall flow diagram of the production of MMA starting from formalin and propanal with an optional discharge column.

It is further preferred to convey the overhead stream from distillation column I and/or the organic phase from the phase separator I wholly or partially to a distillation column II for fractionation (see FIG. 2). In this distillation column II, separation then takes place into a low-boiling by-product fraction comprising methacrolein and also alkyl isobutyrate and/or alkyl propionate, and into an alkyl methacrylate-containing fraction in the bottoms comprising a respective content of methacrolein, alkyl isobutyrate and alkyl propionate of less than 0.1% by weight.

Also preferably, at least one alkyl methacrylate-containing bottom fraction from distillation column I or from distillation column II is conveyed to a distillation column III for removal of high-boiling constituents. Optionally, this fraction purified by high-boilers can then be further purified in a further distillation column for removing further low-boiling constituents (not part of the attached scheme).

Optionally, the distillation in distillation column I can be carried out in the presence of an additional solvent that functions as entrainer.

In one particular version of the present invention, the overhead fraction of distillation column I and/or the aqueous phase of the phase separator I is conveyed into a reactor IV. An acidic hydrolysis takes place in this reactor IV.

It is also preferred to feed the product stream from reactor IV wholly or partially for disposal and/or to recycle it to one of the upstream processing steps.

It has proven to be particularly favourable to operate distillation column I and the optional distillation column II in each case at an absolute pressure between 0.1 bar and 1 bar.

A particularly preferred variant of the process according to the invention is also characterized in that, prior to introduction into distillation column I, extractive separation in an extraction I takes place. In this extractive separation, a fraction comprising water and alkali metal and/or alkaline earth metal salts is separated off. One process option is the distillation of the organic phase of extraction I in a distillation column IV to remove high-boilers from the crude MMA. The high-boiling bottom fraction obtained can then be distilled again in a distillation column V. To minimize MMA losses, the distillate of distillation column V can be recycled to distillation column IV. The distillate of distillation column IV in this process variant is the feed to distillation column I.

The propionaldehyde content of the methacrolein from process step a is preferably between 100 ppm by weight and 2% by weight. Likewise, the content of alkyl isobutyrate in the alkyl methacrylate from process step c is preferably below 2000 ppm.

Distillation stage I, which takes the form of a low-boiler column, can be designed in different ways in order to achieve the required removal of the specified by-products alkyl propionate and alkyl isobutyrate and also the remaining methacrolein. For instance, it has proven to be practicable to use a multi-stage distillation column with decanter in the distillate. The distillation column is generally operated at an internal pressure between 100 mbar and 1 bar, preferably between 150 and 500 mbar and particularly preferably between 200 and 400 mbar. Here, bottom temperatures arise that are at around 55 to 100° C. Since at higher temperatures secondary reactions may occur, for example polymerization, it is advisable to adjust the pressure such that the bottom temperature is below 80° C., preferably below 70° C. The column is preferably designed and operated such that the top temperature is 7 to 15° C. lower than the bottom temperature.

The feed stream in this case predominantly consists of the alkyl methacrylate, preferably MMA, the alkyl isobutyrate, preferably MIB, the alkyl propionate, preferably MP, methacrolein, methanol, water and further low-boilers.

The column preferably comprises 30 to 100, preferably 45 to 65 theoretical plates. A theoretical plate is a local thermodynamic equilibrium within the column. The number of these can also be achieved in two different ways or combinations thereof within one column. These modifications ultimately also result in the required length or the column. Sieve trays can be present in the column. As second or additive method, random packings or structured packings may be filled in regions of the column. The feed to distillation column I can preferably be effected—as seen from the bottom of the column—between the bottom and the middle of the column. The feed is particularly preferably effected between the first third and the middle of the column.

Generally, distillation column I is operated at relatively high reflux-to-feed ratios in the range of 0.5 to 5.0, preferably 1.0 to 3.0.

The purified MMA accrues in the bottom of the column. Here, the operating conditions of the column can be adjusted to the respective processing concept. As a general rule, low-bolters, which are present in this MMA, cannot be separated by columns for high-boiler removal, but are also found again in the end product.

After distillation column I, the distillate is subjected to a phase separation with optional addition of water and here an aqueous and an organic stream are generated. The phase separator can be operated at a temperature below 50° C. The temperature is preferably between 4 and 30° C., generally between 15 and 25° C. The water-to-feed ratio at the phase separator is generally between 0 (no additional water) and 0.5, preferably between 0.1 and 0.2. The aqueous stream mainly comprises $H_2O$, methanol and a certain proportion of the organic substances MMA, MP, MIB, etc. The aqueous stream is either treated as wastewater or can be subjected to an optional by-product treatment, such as an acidic hydrolysis. In the case of acidic hydrolysis, generally with addition of an inorganic acid, MMA, MP and MIB are resaponified. In this case, this saponification is controlled with respect to temperature, acid concentration and residence time in reactor IV such that the saponification is incomplete overall. Since the saponification reactions of MP and MIB are kinetically preferred compared to MMA, in this way, a relevant proportion of MMA may remain. Eliminated methanol and remaining MMA can alternatively be subsequently isolated, e.g. by distillation, without much effort. Optionally, the total product from reactor IV can be conveyed to distillation column VI, which is the so-called methanol recovery column. Owing to the high boiling point of the free acids, isobutyric acid and propionic acid can then be simply fed via the bottoms of distillation column VI to wastewater processing.

The organic stream of phase separator I is wholly fed to the column or it is optionally withdrawn as a discharge stream. Optionally, this discharge stream can be purified in a further column. In this case, MMA is recovered as bottom product and the low-boilers to be removed (MIB, MP, MAL) separated off as distillate.

It should be noted for the sake of completeness that everything in the preceding paragraphs concerning methanol, MMA, MP and MIB is naturally also transferable to other alcohols and thus alkyl methacrylates, alkyl isobutyrates and alkyl propionates.

The process according to the invention permits the removal of methyl isobutyrate and at the same time the removal of methacrolein and methyl propionate in a single distillation column with simultaneous MMA recovery rates of over 99% by weight.

EXAMPLES

Example 1

In a continuously operating plant, shown in FIG. 1, the distillate stream (31) of the high-boiler column (distillation column IV) (28) is produced, which is purified of the low-boilers by distillation in the subsequent low-boiler column (distillation column I) (32). By means of the operation, an MMA bottom stream containing process stabilizers can be produced having an MP content <10 ppm and an MIB content <350 ppm.

The low boiler column is operated at an operating pressure of 250 mbar absolute. The column is equipped with the structured packing M750.Y from Sulzer (diameter 100 mm, packing height 12,000 mm, feed at 8000 mm). Process stabilizers are added to the condensers. The process stabilizer is dissolved in MMA and the addition rate is 330 g/h. A phase separator, which is temperature-controlled at an operating temperature of 20° C. and has a water feed (34), generates an aqueous phase (38) and an organic phase. The organic phase is recycled to the column as return flow and is partially discharged from the process as discharge stream (35).

In the present example, the distillate stream (31) of the high-boiler column is 11,000 g/h and comprises 98.0% by weight MMA, 1.0% by weight $H_2O$, 0.2% by weight MAL, 0.1% by weight MP, 0.1% by weight MIB and 0.5% by weight residue, wherein this residue is predominantly methanol. A reflux-to-feed ratio of 1.1 Is set and the discharge stream is fixed at 112 g/h. The water addition rate in the phase separator is 1285 g/h. This results in a head temperature of 53° C. and a bottom temperature of 61° C. The aqueous stream (36) of the phase separator is 1483 g/h and comprises 1.2% by weight MMA, 93.8% by weight $H_2O$, 1% by weight MAL, 0.3% by weight MP, 0.1% by weight MIB and 3.6% by weight residue. This results in a bottoms output (40) of 10,950 g/h with the composition 99.9% by weight MMA, 50 ppm MP, 350 ppm MIB and 0.06% by weight process stabilizer. In the operating mode shown, an MMA retention of 99.04% was achieved.

Example 2

Using the column (operating pressure of 250 mbar absolute) and the phase separator (operating temperature 20° C.) of example 1, the distillate stream (31) of the high-boiler column (11,000 g/h, comprises 96.7% by weight MMA, 1.8% by weight $H_2O$, 0.1% by weight MAL, 0.1% by weight MP, 0.2% by weight MIB and 1.1% by weight residue) is distilled. In this case, the reflux-to-feed ratio is set at 2.2 and the discharge stream is fixed at 25 g/h. The water addition rate in the phase separator is 1530 g/h. This results in a head temperature of 54° C. and a bottom temperature of 62° C. The aqueous stream (36) of the phase separator is 1858 g/h and comprises 1.6% by weight MMA, 91.8% by weight $H_2O$, 0.4% by weight MAL, 0.4% by weight MP, 0.5% by weight MIB and 4.9% by weight residue. The bottoms output (40) is 11,035 g/h with the composition 99.91% by weight MMA, 35 ppm MP, 315 ppm MIB and 0.06% by weight process stabilizer. This mode of operation described achieves an MMA retention of 99.71%.

Example 3

In the column (operating pressure of 250 mbar absolute) and the phase separator (operating temperature 20° C.) of example 1, the distillate stream (31) of the high-boiler column (11,000 g/h, comprises 96.7% by weight MMA, 1.8% by weight $H_2O$, 0.1% by weight MAL, 0.1% by weight MP, 0.2% by weight MIB and 1.1% by weight residue) is distilled. In this case, the reflux-to-feed ratio is set at 2.0 and the discharge stream is fixed at 25 g/h. There is no water addition to the phase separator. This results in a head temperature of 50° C. and a bottom temperature of 62° C. The aqueous stream (36) of the phase separator is 335 g/h and comprises 5.5% by weight MMA, 60.0% by weight $H_2O$, 2.0% by weight MAL, 1.5% by weight MP, 2.0% by weight MIB and 29.0% by weight residue. The bottoms output (40) is 11,000 g/h with the composition 99.9% by weight MMA, 55 ppm MP, 320 ppm MIB and 0.06% by weight process stabilizer. An MMA retention of 99.51% is achieved.

Example 4

The process arrangement applied in Examples 1 to 3 is supplemented by a further distillation column II (44), the so-called discharge column (FIG. 2). The discharge stream (35) is supplied to this column as feed and purified by distillation. The distillate (45) generated comprises in this case the low-boiling components (MAL, MP and MIB). The bottom fraction comprises MMA with process stabilizer and is recycled to the low-boiler column. The discharge column is operated at a pressure of 250 mbar absolute. The column is equipped with the high performance laboratory packing DX from Sulzer (diameter 50 mm, packing height 2000 mm). The operating conditions of the low-boiler column and the phase separator are the same as Example 1. The feed to the low-boiler column is 11,000 g/h and comprises 96.7% by weight MMA, 1.8% by weight $H_2O$, 0.1% by weight MAL, 0.1% by weight MP, 0.2% by weight MIB and 1.1% by weight residue. In this case, the reflux-to-feed ratio is set at 1.0 and the water addition rate to the phase separator is 1530 g/h. This results in a head temperature of 54° C. and a bottom temperature of 62° C. The discharge stream (35), which functions as reed to the discharge column. Is fixed at 110 g/h. The aqueous stream (38) of the phase separator is 1858 g/h and comprises 1.2% by weight MMA, 93.8% by weight $H_2O$, 1% by weight MAL, 0.4% by weight MP, 0.1% by weight MIB and 3.5% by weight residue. The head temperature of the discharge column is 34° C. and a bottom temperature of 61° C. A distillate stream (45) of the discharge column is obtained of 22 g/h comprising 2.1% by weight MMA, 7.9% by weight $H_2O$, 39.9% by weight MAL, 26.6% by weight MP, 19.5% by weight MIB and 4.0% by weight residue. The bottom (46) of the discharge column is fully recycled to the low-boiler column. This results in a bottoms output (40) of the low-boiler column of 11,038 g/h with the composition 99.91% by weight MMA, 5 ppm MP, 315 ppm MIB and 0.06% by weight process stabilizer. The MMA retention is 99.73%.

Example 5

The process arrangement applied in Example 1 is supplemented by a stirred tank reactor (reactor IV) (37) having a reactor volume of 250 ml (FIG. 1). The stirrer is operated at 500 rpm and the operating temperature is 40° C. The aqueous phase (38) of the phase separator is conveyed into this reactor (37). This stream consists of 1.2% by weight MMA, 93.8% by weight $H_2O$, 1% by weight MAL, 0.3% by weight MP, 0.1% by weight MIB and 3.6% by weight residue and is obtained at a rate of 1483 g/h. In addition, 9.8 g/h of 96% sulfuric acid (38) is added to the stirred tank reactor (37). A residence time of 10 min results from the flows described. In this case, an MP conversion of 44%, MIB conversion of 48% and an MMA conversion of 44% is determined.

Example 6

Using the column (operating pressure of 600 mbar absolute) and the phase separator (operating temperature 20° C.)

of example 1, the distillate stream (31) of the high-boiler column (11,000 g/h, comprises 96.7% by weight MMA, 1.8% by weight H$_2$O, 0.1% by weight MAL, 0.1% by weight MP, 0.2% by weight MIB and 1.1% by weight residue) is distilled. Hexane is added to the top of the column as entrainer. The hexane loss to be compensated is 8.8 g/h. In this case, the reflux-to-feed ratio is set at 1.8 and the discharge stream is 73 g/h. The water addition rate in the phase separator is 1489 g/h. This results in a head temperature of 54° C. and a bottom temperature of 84° C. At the top of the column, a hexane content of 60.5% by weight is achieved. The aqueous stream (38) of the phase separator is 1816 g/h and comprises 0.4% by weight MMA, 92.9% by weight H$_2$O, 0.4% by weight MAL, 0.4% by weight MP, 0.4% by weight MIB and 5.5% by weight residue. The bottoms output (40) is 10,930 g/h with the composition 99.90% by weight MMA, 35 ppm MP, 315 ppm MIB and 0.07% by weight process stabilizer. This mode of operation described achieves an MMA retention of 99.66%.

LIST OF REFERENCE SIGNS

FIG. 1 Overall flow diagram of the production of MMA starting from formalin and propanal.

FIG. 2 Overall flow diagram of the production of MMA starting from formalin and propanal with optional discharge column (1) Formalin feed to reactor I
(2) Propanal feed to reactor I
(3) Optional stabilizer feed to reactor I
(4) Reactor I for methacrolein synthesis
(5) Processing of the crude methacrolein
(6) Methacrolein feed to reactor II
(7) Reactor II for oxidative esterification of methacrolein
(8) Alcohol feed (normally methanol feed)
(9) Oxygen/air inflow line
(10) Base feed
(11) Reactor II offgas
(12) Reactor II reactor output
(13) Distillation column VII: methacrolein recovery column
(14) MAL recycling
(15) MAL acetal converter
(16) Acid feed (normally sulfuric acid)
(17) MAL acetal converter product stream
(18) Extraction I
(19) Water feed for extraction I
(20) Aqueous phase of extraction I
(21) Distillation column VI: methanol recovery column
(22) Low-boiling fraction comprising alcohol for recycling to reactor II
(23) Recycling to the methanol recovery column
(24) Bottom fraction comprising water, acid and alkali metal salts thereof, for disposal or further processing,
(25) Organic phase or the extraction
(26) Distillation column IV: high-boiler column
(27) Bottom fraction comprising MMA, methacrylic acid and high-boilers
(28) Distillation column V: MMA recovery column
(29) Distillate comprising MMA
(30) Bottom fraction comprising methacrylic acid and high-boilers
(31) Distillate comprising MMA and low-boilers
(32) Distillation column I: low-boiler column
(33) Optional phase separator I
(34) Optional water addition
(35) Optional discharge stream
(38) Optional aqueous phase of phase separator I
(37) Optional reactor IV acidic hydrolysis
(38) Acid feed (normally sulfuric acid)
(39) Product stream of acidic hydrolysis, optionally as recycling stream
(40) Bottom fraction of low-boiler column
(41) Distillation column III: MMA pure column for final purification of MMA
(42) Specification-compliant MMA as distillate of MMA pure column
(43) Bottom fraction of MMA pure column optional recycling to high-boiler column
(44) Distillation column II: discharge column
(45) Distillate comprising low-boilers such as methyl isobutyrate and methyl propionate
(46) Bottom fraction of discharge column comprising MMA
(A) Offgas The figures represent by way of example two different versions of the present invention.

The invention claimed is:

1. A process for producing alkyl methacrylates, the process comprising:
   a. producing methacrolein in a first reaction stage in a reactor I, from propionaldehyde and formalin, wherein the methacrolein comprises remaining propionaldehyde,
   b. oxidatively esterifying the methacrolein with an alcohol in the presence of an oxygen-containing gas in a second reaction stage in a reactor II, to obtain a crude alkyl methacrylate stream, and wherein in the reactor II and an optional reactor III, the remaining propionaldehyde is converted to alkyl propionate, and optionally alkyl isobutyrate is formed in the reactor II and/or the optional reactor III,
   c. after the reactor II or the optional reactor III, the crude alkyl methacrylate stream, comprising the alkyl propionate and optionally the alkyl isobutyrate, is processed in a work-up process to give pure alkyl methacrylate by two or more distillative separation columns and at least one extractive separation, the two or more distillative separation columns comprising a distillation column I, in which, by fractionation, the pure alkyl methacrylate is separated off as a bottom fraction, and a by-product fraction, comprising the methacrolein, the alkyl isobutyrate, and the alkyl propionate, is obtained as an overhead fraction.

2. The process according to claim 1, wherein the pure alkyl methacrylate from process step c is obtained having a respective content of the alkyl propionate and the alkyl isobutyrate of less than 0.1% by weight.

3. The process according to claim 1, wherein the overhead fraction from the distillation column I is conveyed to a phase separator I and is separated therein into an aqueous fraction and an organic fraction.

4. The process according to claim 3, wherein additional water is conveyed into the phase separator I, wherein the additional water is fresh water and/or a water-containing recycling stream from one or more other process steps.

5. The process according to claim 3, wherein the organic fraction from the phase separator I comprises the methacrolein, the alkyl isobutyrate, and the alkyl propionate, and is partially or wholly recycled to the distillation column I.

6. The process according to claim 3, wherein the overhead fraction of distillation column I and/or the organic fraction from the phase separator I is wholly or partially conveyed to a distillation column II for fractionation, and is separated in the distillation column II into a low-boiling by-product fraction comprising the methacrolein, the alkyl isobutyrate, and/or the alkyl propionate, and into an alkyl methacrylate-containing fraction in a bottom comprising a respective content of the methacrolein, the alkyl isobutyrate, and the alkyl propionate of less than 0.1% by weight.

7. The process according to claim 6, wherein at least one alkyl methacrylate-containing bottom fraction from the distillation column I or from the distillation column II is further purified in a distillation column III for removal of high-boiling constituents, and is thereafter conveyed to an optional distillation column for removal of further low-boiling constituents.

8. The process according to claim 1, wherein distillation in the distillation column I is carried out in the presence of an additional solvent that functions as an entrainer.

9. The process according to claim 3, wherein the overhead fraction from the distillation column I or the aqueous fraction from the phase separator I is conveyed to a reactor IV in which an acidic hydrolysis is carried out.

10. The process according to claim 9, wherein a product stream from the reactor IV is wholly or partially fed for disposal and/or is recycled to an upstream processing step.

11. The process according to claim 6, wherein the distillation column I and optionally, the distillation column II, are each operated at an absolute pressure between 0.1 bar and 1 bar.

12. The process according to claim 1, wherein prior to introduction into the distillation column I, the at least one extractive separation is carried out, in an extraction I, in which a fraction comprising water and alkali metal and/or alkaline earth metal salts is separated off.

13. The process according to claim 1, wherein a propionaldehyde content of the methacrolein from process step a is between 100 ppm and 2% by weight.

14. The process according to claim 1, wherein a content of the alkyl isobutyrate in the pure alkyl methacrylate from process step c is below 2000 ppm.

15. The process according to claim 1, wherein the alcohol is methanol, the alkyl methacrylate is methyl methacrylate, the alkyl isobutyrate is methyl isobutyrate, and the alkyl propionate is methyl propionate.

* * * * *